United States Patent [19]

Sandler et al.

[11] Patent Number: 4,906,280
[45] Date of Patent: Mar. 6, 1990

[54] TERTIARY BUTYLHYDRAZIDES AS PLANT GROWTH REGULATORS

[75] Inventors: Stanley R. Sandler, Springfield, Pa.; Shyam B. Advani, Peoria, Ariz.

[73] Assignee: Pennwalt Corporation, Philadelphia, Pa.

[21] Appl. No.: 108,409

[22] Filed: Oct. 14, 1987

[51] Int. Cl.$^4$ .................. A01N 43/74; C07C 101/42
[52] U.S. Cl. ............................. 71/90; 71/88; 71/113; 71/115; 548/214; 549/463; 562/439; 562/507; 562/560
[58] Field of Search .............. 71/113, 115, 90, 88; 562/560, 507, 439; 260/544 L, 544 D, 544 N; 548/214; 544/463

[56] References Cited

U.S. PATENT DOCUMENTS

| | | | |
|---|---|---|---|
| 2,859,243 | 11/1958 | Reed | 562/560 |
| 3,240,799 | 3/1966 | Hageman | 71/113 |
| 3,277,111 | 10/1966 | Hageman | 71/113 |
| 3,458,304 | 7/1969 | Hageman | 562/560 |
| 3,759,909 | 9/1973 | Hageman | 71/113 |
| 3,991,112 | 11/1976 | Donnell | 71/113 |

FOREIGN PATENT DOCUMENTS 46-29754  8/1971  Japan ..................... 71/113

OTHER PUBLICATIONS

Allinger, "Organic Chemistry," pp. 529–531, (1971).

*Primary Examiner*—Michael L. Shippen

[57] ABSTRACT

T-butylhydrazides of carboxylic acid anhydrides and carboxylic acid chlorides useful as plant growth regulants in the free acid form or their equivalent salts.

11 Claims, No Drawings

TERTIARY BUTYLHYDRAZIDES AS PLANT GROWTH REGULATORS

BACKGROUND OF THE INVENTION

The present invention provides novel compounds useful as plant growth regulants.

The compounds of the invention are t-butylhydrazides of carboxylic acid anhydrides and carboxylic acid chlorides. The acids may be used as plant growth regulants in the form of free acids or their equivalent salts, i.e., alkali metal, ammonium, or amine.

SUMMARY OF THE INVENTION

The compounds of the invention are of the formula

RNHNR$^1$C(CH$_3$)$_3$ where R and R$^1$, which can be the same or different, are independently selected from the group of radicals consisting of

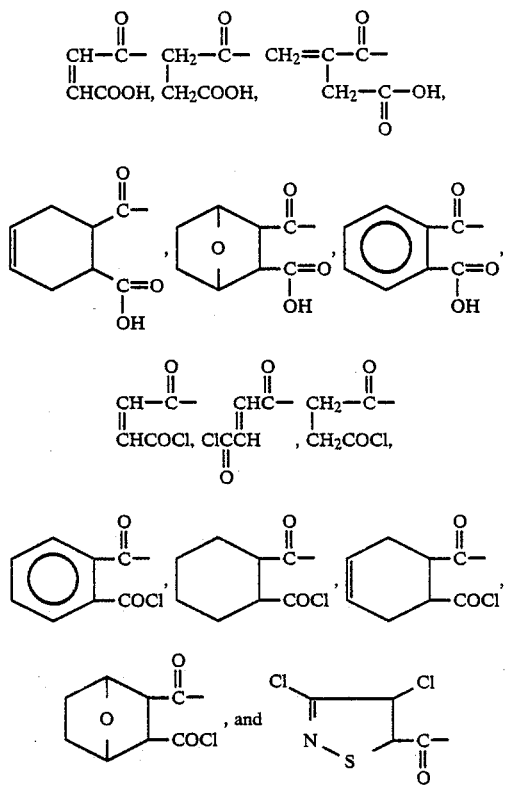

and the alkali metal or ammonium salts of each of the aforegoing carboxy containing radicals, with the proviso that R$^1$ can also be hydrogen.

The preferred compounds are as above defined wherein R$^1$ is hydrogen.

Method of preparing the above novel compounds comprises subjecting a mixture (i) of the corresponding carboxylic acid anhydride or chloride of R and/or R$^1$ (except where R$^1$ is H) and (ii) (CH$_3$)$_3$CNHNH$_2$.HCl, wherein R and R$^1$ are as defined above, to reaction conditions to provide the compound of the invention.

The plant growth regulant composition of the invention comprises a plant growth regulating effective amount of the compound as above defined in admixture with agricultural adjuvants and carriers.

The method of use of the invention comprises treating plants with a plant growth regulating effective amount of the compound of the invention.

DETAILED DESCRIPTION OF THE INVENTION

The compounds of this invention are prepared by reacting t-butylhydrazine hydrochloride with the carboxylic acid anhydride or chlorides. For example:

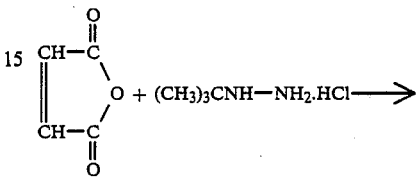

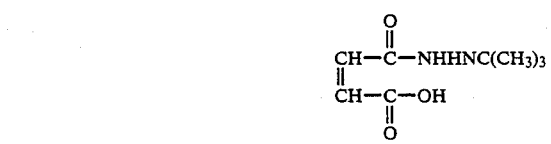

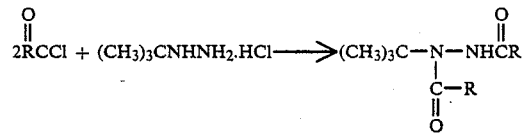

and/or

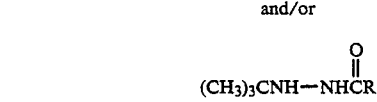

(when less than a stoichiometric amount of the chloride is reacted.)

Specific illustrative examples of the preparation of the compounds of the present invention are shown in Examples 1 to 3.

If R and R$^1$ are to be different (R$^1$ other than H), a mixture of the corresponding anhydrides or chlorides could be used. Optionally, the anhydride or chloride of R could first be reacted and then the anhydride or chloride of R$^1$ added and reacted.

The acids may be used as plant growth regulants in the form of the free acids or their equivalent salts, such as the alkali salts, i.e. alkali metal, ammonium or amine (substituted ammonium) salts, e.g., sodium, potassium, ammonium, methyl ammonium, dimethyl ammonium, trimethyl ammonium, ethyl ammonium, ethanol ammonium, diethanol ammonium, or triethanol ammonium salts, since the salts give equivalent results. The salts may readily be formed directly from the acid and a selected base such as an alkali-metal hydroxide or carbonate, or ammonia, or an amine.

In the general formula for the compounds of the invention:

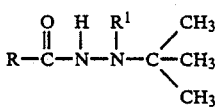

R is derived from C$_4$ to C$_{12}$ mono heterocyclic carboxylic acids or chlorides and C$_4$ to C$_{12}$ dicarboxylic acids or chlorides. $R^1$ is hydrogen or derived from a heterocyclic substituted carboxylic acid or chloride.

Other substituents for R and $R^1$ are also possible. Other heterocyclic or aromatic dicarboxylic acid anhydrides can be used in the method disclosed in this invention to prepare the respective t-butylhydrazide derivatives. For example, dicarboxylic anhydrides that are useful are maleic anhydride, succinic anhydride, itaconic acid anhydride, tetrahydrophthalic anhydride, 3,6-endoxohexahydrophthalic anhydride, phthalic anhydride and related diacid anhydrides. Dicarboxylic acid chlorides which are useful are maleic acid chloride, fumaroyl chloride, succinoyl chloride, phthaloyl chloride, hexahydrophthaloyl chloride, tetrahydrophthaloyl chloride, 3,6-endoxohexahydrophthaloyl chloride and related compositions. Monoacid chlorides that are useful are those derived from 3,4-dichloroisothiazole 5-carboxylic acid and related compositions.

EXAMPLE 1

Preparation of the Mono t-Butylhydrazide of Maleic Acid

To a three necked flask equipped with a mechanical stirrer and condenser were added 9.8 g (0.1 mole) of maleic anhydride, 12.4 g (0.1 mole) of t-butylhydrazine hydrochloride and 10.6 g (0.1 mole) of solid sodium carbonate and 200 ml of toluene. The mixture was refluxed for eight hours; cooled and filtered to give 33.6 g of a solid. The latter solid product was purified by washing with acetone (1 liter). Concentration of the acetone extract gave 1.1 g of solid product, m.p. 151°–152° C.

Analysis calculated for:

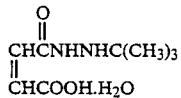

$C_8H_{16}N_2O_4$: C, 47.1%; H, 7.8%; N, 13.7%, Found: C, 47.7%; H, 7.0%; N, 13.7%.

The infrared spectrum was consistent with the above structure.

EXAMPLE 2

Preparation of the Mono t-Butylhydrazide of Succinic Acid

To a flask as described in Example 1 were added 10.0 g (0.1 mole) of succinic anhydride, 10.6 g (0.1 mole) of sodium carbonate and 250 ml acetonitrile. The mixture was stirred while 12.4 g (0.1 mol) of t-butylhydrazine hydrochloride was added. The mixture was stirred and heated to refluxing for 24 hours. The reaction mixture was cooled and filtered to give an oily solid which was washed with acetone to give 1.4 g of solid, m.p. 131°–132° C. The acetone filtrates were concentrated to give 8.9 g of a semi-solid whose infrared spectrum was identical to the 1.4 g solid. The product is slightly hygroscopic. Analysis calculated for:

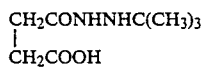

$C_8H_{16}N_2O_3$: C, 51.1; H, 8.5; N, 14.9, Found: C, 49.9; H, 8.6; N, 14.5.

The infrared spectrum was consistent with the above structure.

EXAMPLE 3

Preparation of the N-t-butyl; 3,4-dichloro-5-isothiazole carboxylate disubstituted Hydrazide To a flask equipped as in Example 1 were added 11.0 g (0.05 mole) of 3,4-dichloro-5-isothiazole-carboxylic acid chloride, 6.2 g (0.05 mole) of t-butylhydrazine hydrochloride, 5.3 g (0.05 mole) of sodium carbonate and 200 ml of toluene. The mixture was heated to 60° C. for six hours. To this was then added 5 g. (0.05 mole) of triethylamine and then stirred overnight at room temperature. The mixture was filtered and the filtrate concentrated under reduced pressure to obtain a semi-solid which on treatment with ether gave 1.5 g of the solid product, m.p. 174°–176° C. Analysis calculated for:

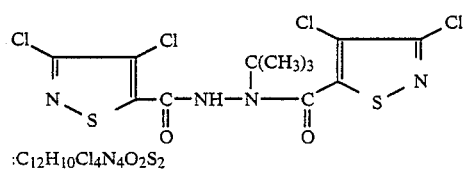

$:C_{12}H_{10}Cl_4N_4O_2S_2$

The infrared spectrum was consistent with the above structure.

EXAMPLE 4

This describes the testing of the compounds from Examples 1 to 3 on bean plants.

Procedure

Different microliter amounts of each derivative (applied as a 1000 ppm emulsifiable concentrate) were pipetted onto both primary leaves of *Phaseolus vulgaris* (Black Valentine Bean) plant. Each replicate consisted of four plants, three of which received different amounts and one that acted as a pot control. There were four replicate pots. Application occurred prior to a trifoliate growth length of 10 mm. After application, internode length was measured on a dialy basis until the same measurement was obtained on three consecutive days. Growth rate data was obtained by taking the derivative of the elongation curve with respect to time. These data were then substracted from the pot control data to provide the relative rate of elongation with respect to the control. To determine differences between application concentrations, the Kruskal-Wallis test was applied.

The results, which are summarized in Table I, show that growth regulating activity is present in varying degrees with the derivatives. The activity of each derivative is discussed below.

TABLE I

| | Relative Internodal Elongation Rate | | | |
| --- | --- | --- | --- | --- |
| | Average Deviation from Control (mm/day)- Relative Internodal Elongation Rate | | | |
| Concentrations µg/leaf | Example 1 | Example 2 | Example 3 | Alar Control |
| 6.0 | +0.5 | +1.6 | +5.5 | +2.7 |
| 12.5 | −6.3 | +4.5 | −1.75 | +2.5 |
| 25.0 | +0.5 | +4.75 | +1.5 | +3.0 |
| 50.0 | −3.0 | −0.25 | −1.0 | −2.5 |
| 100.0 | −6.5 | +1.25 | +0.25 | −2.75 |
| 200.0 | −4.5 | +0.10 | −4.25 | −6.0 |

The compound of Example 1 shows the most promise. Except for the large negative deflection at 12.5 µg/leaf (resulted from one replicate that grew exceptionally fast) the activity profile is similar to that of Alar ®. (Note that statistical significance was not assigned to ratio higher than 50 µg/leaf because of the large degree in variability attributed to the aforementioned atypical plant.) Inhibitory activity which was similar to Alar ® is observed between 25–50 µg/leaf (Table I). Local droplet chlorosis ranged from mild to severe (Table II).

The compound of Example 2, a derivative of succinic acid, provided some increased growth at lower rates but showed no significant growth retardant activity in the range of Alar ®. Because the rate of internode elongation approached that of the control between 50–200 µg/leaf, this may signify that the inhibitory action may begin just outside the test range (Table I). Local chlorosis at the site of application was mild (Table II).

The compound of Example 3 dramatically affected plant growth by inhibiting photosynthesis. Phytotoxicity, manifested as local tissue necrosis, was proportional to the total volume of solution pipetted onto each leaf. (See Table II.) A growth enhancement effect was observed at the lowest rate and volume of application which indicates that the derivative is influencing the growth rate at minimum tissue damage. (Note that all drops caused local tissue necrosis but that overal *leaf* necrosis and internode inhibition was related to the number of drops per leaf).

With the Alar ® Control of Example 4, concentrations of 25 µg/leaf or lower stimulated the rate of internode enlongation. Conversely, concentrations of 50 µg/leaf or greater show a significant reduction in internode elongation. This stimulatory/inhibitory function is common for many growth regulators and is generally a function of concentration. Consequently, Alar's effective concentration is between 25–50 µg/leaf. No chlorosis was observed. (Table II.)

TABLE II

Phytotoxicity Associated With Tertiary Butyl Hydrazine Compounds Applied at a Concentration of 1000 ppm to Phaseolus vulgaris

| Compound I.D. | Structure | Phytotoxicity* at Designated Rates (µg/leaf) | | | | | |
|---|---|---|---|---|---|---|---|
| | | 6 | 12.5 | 25.0 | 50.0 | 100.0 | 200.0 |
| Alar ® | $CH_3\!\!>\!\!N\text{-}NH\text{-}C(=O)\text{-}CH_2\text{-}CH_2\text{-}C(=O)\text{-}OH$ (with two $CH_3$) | 1 | 1 | 1 | 1 | 1 | 1 |
| Example 1 | $CH\text{=}C(\text{-}NHNHC_4H_9)\text{-}C(\text{=}O)\text{-}...$ maleic hydrazide derivative | 1.5 | 2.3 | 2.8 | 2.8 | 3.0 | 3.8 |
| Example 2 | $CH_2\text{-}C(=O)\text{-}NHNH\cdot TBU$, $CH_2\text{-}C(=O)OH$ | 1.8 | 2.0 | 2.5 | 3.0 | 2.5 | 2.5 |
| Example 3 | dichlorothiazole-C(=O)-NH-N(t-Bu)-C(=O)-dichlorothiazole | 5 | 4.7 | 6.3 | 6.5 | 7.7 | 9.0 |

*Score under the EWRS classification scale: 1, no symptoms/healthy plants: 2, very mild symptoms, slight stunting; 3, mild but clearly recognizable symptoms; 4, more severe symptoms (e.g., chlorosis) not necessarily with negative effect on yield; 5, thinning out, heavy chlorosis or stunting, reduction in the yield to be expected; 6–9, heavy damage to total kill.

I claim:
1. A compound of the formula

RNHNR$^1$C(CH$_3$)$_3$ where R and R$^1$, which can be the same or different, are independently selected from the group of radicals consisting of

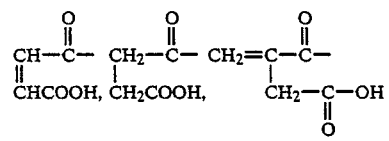

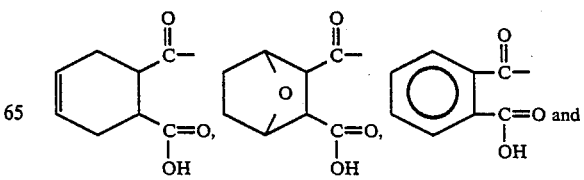

and

-continued

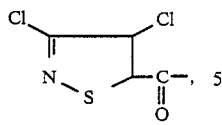

and the alkali metal or ammonium salts of each of the aforegoing carboxy containing radicals, with the proviso that $R^1$ can also be hydrogen.

2. The compound of claim 1 wherein $R^1$ is hydrogen and R is

3. The compound of claim 1 wherein $R^1$ is hydrogen.

4. The compound of claim 3 wherein R is selected from the group consisting of

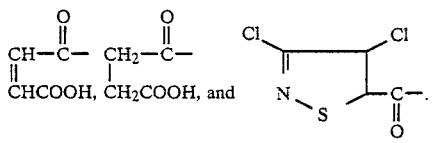

5. A plant growth regulating composition comprising a plant growth regulating compound of the formula $$RNHNR^1C(CH_3)_3$$

where R and $R^1$ are the same or different radicals selected from the group consisting of

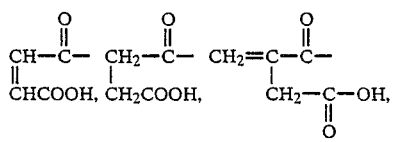

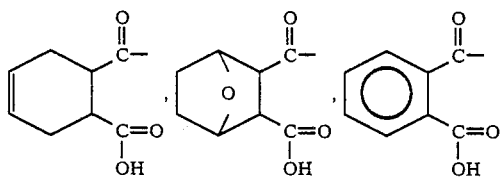

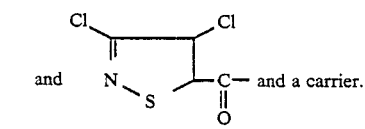
and a carrier.

6. The composition of claim 5 wherein $R^1$ is hydrogen and R is selected from the group consisting of

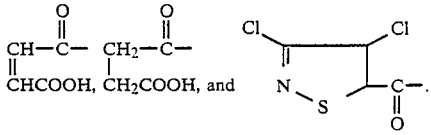

7. The composition of claim 5 wherein $R^1$ is hydrogen and R is

8. A method for regulating plant growth which comprises treating the plants with a plant growth regulating effective amount of a compound of the formula $$RNHNR^1C(CH_3)_3$$

where R and $R^1$ are the same or different radicals selected from the group consisting of

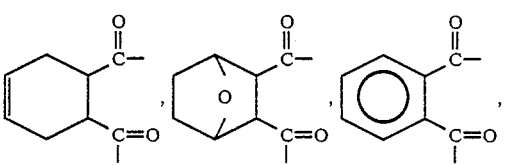

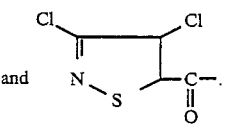

9. The method of claim 8 wherein $R^1$ is hydrogen.

10. The method of claim 8 wherein $R^1$ is hydrogen and R is selected from the group consisting of

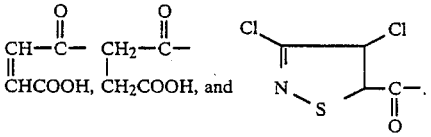

11. The method of claim 8 wherein $R^1$ is hydrogen and R is

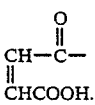

* * * * *